US005880153A

United States Patent [19]
Neuman et al.

[11] Patent Number: 5,880,153
[45] Date of Patent: Mar. 9, 1999

[54] METHOD FOR UPREGULATION OF TRKB AND TRKC RECEPTORS IN CENTRAL NERVOUS SYSTEM NEURONS

[75] Inventors: Toomas Neuman, Fort Collins, Colo.; Henry Connor, Absarokee, Mont.; Howard O. Nornes, Fort Collins, Colo.

[73] Assignee: Spinal Cord Society, Fergus Falls, Minn.

[21] Appl. No.: 747,490

[22] Filed: Nov. 12, 1996

[51] Int. Cl.$^6$ .................................................. A61K 31/19
[52] U.S. Cl. ........................................................ 514/557
[58] Field of Search ............................................ 514/557

[56] References Cited

PUBLICATIONS

Knusel et al., "Brain–derived Neurotrophic Factor Administration Protects Basal Forebrain Cholinergic But Not Nigral Dopaminergic Neurons From Degenerative Changes After Axotomy In the Adult Rat Brain", The Journal of Neuroscience, Nov. 1992, 2(11) :4391–4402.

Morse et al., "Brain–Derived Neurotrophic Factor (BDNF) Prevents the Degeneration of Medial septal Cholinergic Neurons Following Fimbria Transection, " The Journal of Neuroscience, Oct. 1993, 13(10) :4146–4156.

Levi–Montalcini et al., "A Diffusible Agent of Mouse Sarcoma, Producing Hyperplasia of Sympathetic Ganglia And Hyperneurotization of Viscera In In The Chick Embryo, " J Exp. Zool, 123:233–288 (1953).

Maisonpierre et al., "Neurotrophin–3: A Neurotrophic Factor Related To NGF And BDNF, " Science, vol. 247, pp. 1446–1451 (1990).

Hohn et al., "Identification and Characterization Of A Novel Member Of The Nerve Growth Factor/Brain–Derived Neurotrophic Factor Family " Nature, vol. 344, 22 Mar. 1990, pp. 339–341.

Hallbrook et al., "Evolutionary Studies Of The Nerve Growth Factor Family Reveal A Novel Member Abundantly Expressed In Xenopus Ovary, " Neuron, vol. 6, pp. 845–858, May, 1991.

Klein et al., "The trk Proto–Oncogene Encodes A Receptor For Nerve Growth Factor, " Cell, vol. 65, pp. 189–197, Apr. 5, 1991.

Kaplan et al., "Tyrosine Phosphorylation and Tyrosine Kinase Activity Of The trk Proto–Oncogene Product Induced By NGF, " Nature, vol. 350, 14 Mar. 1991, pp. 158–160.

Klein et al., "The trk Tyrosine Protein Kinase Is A Receptor For Brain–Derived Neurotrophic Factor And Neurotrophin–3, " Cell, vol. 66, pp. 395–403, Jul. 26, 1991.

Richardson et al., "Peripheral Nerve Autografts To The Rat Spinal Cord: Studies With Axonal Tracing Methods, " Brian Research, 237:147–162 (1982).

Guth et al., "Esentiality of a Specific Cellular Terrain for Growth of Axons into a Spinal Cord Lesion, " Experimental Neurology 88:1–12 (1985).

Nornes et al., "Intraspinal Transplants of Catecholamine–Containing Cells and Fetal Spinal Cord and Iris Tissues in the Adult Rat, " Advances In Neurology, Neuronal Injury and Regeneration, 59:185–197, Ed. FJ Seil, Raven Press, NJ (1993).

Houle, "Demonstration of the Potential for Chronically Injured Neurons to Regenerate Axons into Intraspinal Peripheral Nerve Grafts, " Experimental Neurology 113:1–9 (1991).

Richardson et al., "Axons from CNS Neurones Regenerate Into PNS Grafts, " Nature, vol. 284, Mar. 20, 1980, pp. 264–265.

David et al., "Axonal Elongation Into Peripheral Nervous System Bridges After Central Nervous System Injury In Adult Rats, " Science, vol. 214 20 Nov. 1981, pp. 931–933.

Schnell et al., "Neurotrophin–3 Enhances Sprouting of Corticospinal Tract During Development and After Adult Spinal Cord Lesion, " Nature, vol. 367, 13 Jan. 1994, pp. 170–173.

Verney et al., "Cajal–Retzius Neurons In Human Cerebral Cortex At Midgestation Show Immunoreactivity for Neurofilament and Calcium–Binding Proteins, " The Journal of Comparative Neurology 359:144–153 (1995).

Klein, "Role of Neurotrophins in Mouse Neuronal Development, " The FASEB Journal, vol. 8, Jul. 1994, pp. 738–744.

Yan et al., Brain–Derived Neurotrophic Factor Rescues Spinal Motor Neurons From Axotomy–Induced Cell Death, Nature, vol. 360, 24/31 Dec. 1992, pp. 753–755.

Soppet et al., "The Neurotrophic Factors Brain–Derived Neurotrophic Factor And Neurotrophin–3 Are Ligands For The trkB Tyrosine Kinase Receptor, " Cell, 65: 895–903 (1991).

Squinto et al., "trkB Encodes A Functional Receptor For Brain–Derived Neurotrophic Factor And Neurotrophin–3 But Not Nerve Growth Factor, " Cell, 65:885–893 (1991).

Middlemas et al., "trkB, A Neural Receptor Protein–Tyrosine Kinase:Evidence For A Full–Length And Two Truncated Receptors, " Molecular And Cellular Biology, 11:143–153 (1991).

Lamballe et al., "trkC, A New Member Of The trk Family Of Tyrosine Protein Kinases, Is A Receptor For Neurotrophin–3, " Cell, 66:967–979 (1991).

Sutter et al., "Nerve Growth Factor Receptors, " The Journal of Biological Chemistry, vol. 254, No. 13, pp. 5972–5982 (1979).

Merlio et al., "Molecular Cloning Of Rat trkC and Distribution Of Cells Expressing Messenger RNAs For Members Of The trk Family In The Rat Central Nervous System, " Neuroscience, vol. 51, No. 3, pp. 513–532, 1992.

(List continued on next page.)

Primary Examiner—Keith D. MacMillan
Attorney, Agent, or Firm—Finnegan, Henderson, Farabow, Garrett & Dunner, L.L.P.

[57] ABSTRACT

The present invention provides compositions and methods for inducing expression of neurotrophic factor receptors trkB and trkC in neurons. The compositions include a material that activates a nuclear hormone receptor, a material that activates the second messenger response system, and a material that elevates $Ca^{2+}$.

19 Claims, 6 Drawing Sheets

OTHER PUBLICATIONS

Escandon et al., "Regulation of Neurotrophin Receptor Expression During Embroyonic And Postnatal Devlopment, " The Journal of Neuroscience, Apr. 1994, 14(4) : 2054–2068.

Xu et al., "BDNF And NT–3 Promote Axonal Regeneration Of Brainstem Neurons Into Schwann Cell Grafts In Midthroacic Spinal Cord Of Adult Rats, Proteins", Society For NeuroScience Abstracts, vol. 20, p. 1111, Abstract No. 458.8 (1994).

Kobayashi et al., "Stimulation of GAP–43 and Tα1–Tubulin mRNA Expression By BDNF In Rat Rubrospinal Neurons After Thoracic Axotomy, " Society For Neuroscience Abstracts, vol. 20, p. 697, Abstract No. 296.4 (1994).

Mamounas et al., "BDNF Prevents The Neurotoxin–Induced Loss of 5–HT Axons And Promotes Sprouting Of Uninjured 5–HT Axons In Rat Brain, " Society For Neuroscience Abstracts, vol. 20, p. 441, Abstract No. 193.6 (1994).

Siuciak et al., "Antinocieptive Effect Of Brain–Derived Neurotrophic Factor And Neurotrophin–3, " Brain Research 633: 326–330 (1994).

Frisen et al., "Increased Levels Of trkB mRNA and trkB Protein–Like Immunoreactivity In The Injured Rat And Cat Spinal Cord, " Proc. Natl. Acad. Sci. USA, vol. 89, pp. 11282–11286, Dec. 1992.

Frisen et al., "Characterization Of Glial trkB Receptors: Differential Response To Injury In The Central And Peripheral Nervous System, " Proc. Natl. Acad. Sci., USA, vol. 90, pp. 4971–4975, Jun. 1993.

Ernfors et al., "Expression of mRNAs For Neurotrophin Recpetors In The Dorsal Root Ganglion And Spinal Cord During Development And Following Peripheral Or Central Axotomy, " Molecular Brain Research, 17:217–226 (1993).

Ip et al., "Neurotrophic Factors And Their Receptors, " Ann. Neurol., 35 (Supp):S13–S16 (1994).

Rocamora et al., "Limbic Seizures Induce A Differential Regulation Of The Expression Of Nerve Growth Factor, Brain–Derived Neurotrophic Factor And Neurotrophin–3, In The Rat Hippocampus, " Molecular Brain Research, 13: 27–33 (1992).

Meberg et al., "Induction of F1/GAP–43 Gene: Expression In Hippocampal Granule Cells After Seizures, " Molecular Brain Research, 17:295–299 (1993.

Tarlov et al., "Time Limits For Recovery After Acute Compression In Dogs, " Arch. Neur. Psychiat., 71:271–290 (1954).

Merlio et al., "Increased Production Of The TrkB Protein Tyrosine Kinase Receptor After Brain Insults, " Neuron, vol. 10, pp. 151–164, Feb. 1993.

Kokaia et al., "Coexpression Of Neurotrphins And Their Receptors in Neurons Of The Central Nervous System, " Proc. Natl. Acad. Sci., USA, vol. 90, pp. 6711–6715, Jul. 1993.

Beck et al., "Induction Of Noncatalytic TrkB Neurotrophin Receptors During Axonal Sprouting In The Adult Hippocampus, " The Journal of Neuroscience, 13(9):4001–4014, Sep. 1993.

Sebert et al., "Expression Of mRNA For Neurotrophic Factors And Their Receptors In The Rat Dorsal Root Ganglion And Sciatic Nerve Following Nerve Injury, " Journal of Neuroscience Research, 36: 357–367 (1993).

Funakoshi et al., "Differential Expression Of mRNAs For Neurotrophins And Their Receptors After Axotmoy Of The Sciatic Nerve, " The Journal of Cell Biology, vol. 123, No. 2, pp. 455–465, Oct. 1993.

Ghosh et al., "Requirement For BDNF In Activity–Dependent Survival Of Cortical Neurons, " Science, vol. 263, 18 Mar. 1994, pp. 1618–1623.

Kaplan et al., "Induction of TrkB By Retinoic Acid Mediates Biologic Responsiveness To BDNF And Differentiation Of Human Neuroblastoma Cells, " Neuron, vol. 11, pp. 321–331, Aug. 1993.

Timmusk et al., "Multiple Promoters Direct Tissue–Specific Expression of the Rat BDNF Gene", Neuron, vol. 10, pp. 475–489, Mar. 1993.

Pfeiffer et al., "Differentiation Of A Teratocaricinoma Line: Preferential Development Of Cholinergic Neurons, " The Jouranl of Cell Biology, vol. 88, pp. 57–66, Jan. 1981.

Wrathall et al., "Spinal Cord Contusion In The Rat: Production Of Graded, Reproducible, Injury Groups, " Experimental Neurology, vol. 88, pp. 108–122 (1985).

Gale et al., "Spinal Cord Contusion In The Rat: Behavorial Analysis Of Functional Neurologic Impairment, " Experimental Neurology, vol. 88, pp. 123–134(1985).

Price, "New Perspectives On Alzheimer's Disease, " Amn. Rev. Neurosci. (1986) vol. 9, pp. 489–512.

Altar et al., "Brain–Derived Neurotrophic Factor Augments Rotational Behavior And Nigrostriatal Dopamine Turnover In Vivo, " Proc. Natl. Acad. Sci., USA, vol. 89, pp. 11347–11351, Dec. 1992.

Mitsumoto et al., "Arrest Of Motor Neuron Disease In Wobbler Mice Cotreated With CNTF And BDNF, " Science, vol. 265, pp. 1107–1110, Aug. 1994.

Conner et al., "Induction of Full–Length TrkB And TrkC Expression In The Adult Spinal Chord, " Society of Neuroscience, vol. 21, Abstract No. 422.17 (1995).

Ghosh et al., "Calcium Signaling In Neurons: Molecular Mechanisms And Cellular Consequences, " Science, 269:239–247 (1995).

Maness et al., "The Neurotrophins And Their Receptors: Structure, Function, And Neuropathy, " Neurosc. and Biobehav. Rev., 18:143–159 (1994).

Ernfors et al., "Cells Expressing mRNA For Neurotrophins And Their Receptors During Embryonic Rat Development, " Eur. J. of Neurosc., 4:1140–1158 (1992).

Klein et al., "Expression Of Tyrosine Kinase Receptor Gene trkB Is Confined To The Murine Embryonic And Adult Nervous System, " Devlop, 109:845–850 (1990.

Barron et al., "Quantitative Cytochemistry Of RNA In Axotomized Feline Rubral Neurons, " Brain Res., 130:469–481 (1977).

LeGros et al., "The Projection Of Retina In The Lateral Geniculate Body, " Proc. R. Soc. London (Biol.), 114:291–313 (1934).

Olton, "Dementia: Animal Models Of The Cognitive Impairment Following Damage To The Basal Forebrain Chilinergic System, " Brain Res. Bull., 25: 499–502 (1990).

Barde et al., "Purification Of A New Neurotrophic Factor From Mammalian Brain, " EMBO J., vol. 1:549–553 (1992).

0  1R  1RC  3R  3C  3RC
  TrkB full
  BDNF
  TrkB truncated
FIG. 1

METHOD FOR UPREGULATION OF TRKB AND TRKC RECEPTORS IN CENTRAL NERVOUS SYSTEM NEURONS

This application claims the benefit of U.S. application Ser. No. 08/558,270, entitled Method For Upregulation Of trkB And trkC Receptors In Central Nervous System Neurons, filed Nov. 13, 1995, which was converted from a regular application into a provisional application.

BACKGROUND AND SUMMARY OF THE INVENTION

Several experimental models have failed to demonstrate significant regeneration in the lesioned adult spinal cord[1-5]. Few neurons in the spinal cord regenerate even when provided with a permissive substrate. Analysis of transplantation experiments[6-10] demonstrates that less than 1% of the neurons within the potential pool of neurons regenerate into the transplant. This suggests that promotion of significant regeneration in the spinal cord requires activation of the growth program. Neurotrophins promote growth and differentiation of neurons and have been shown to be involved in both the development and maintenance of the central nervous system (CNS)[11-13]. They are expressed in similar patterns in both developing and regenerating neurons and also rescue neurons following axotomy[14-16].

Nerve Growth Factor (NGF) is a neurotrophic (NT) factor[17]. More than two decades after the discovery of NGF, brain-derived neurotrophic factor (BDNF) was isolated from brain tissue[18]. Using sequence homologies between NGF and BDNF, neurotrophin-3 (NT3)[19,20] and neurotrophin-4 (NT-4) (also called NT-5 or NT-4/5)[21] were subsequently identified and characterized. NT factors mediate their biological effect by binding with high affinity to cell surface glycoprotein receptors. These receptors are encoded by the trk family of protooncogenes. Trk receptor proteins contain an extracellular ligand binding domain and an intracellular tyrosine kinase domain. The extracellular ligand binding domain activates the intracellular tyrosine kinase domain. NGF binds to the trk gene product, gp 140 $^{trk}$(trkA)[22,23]. BDNF and NT-4 bind to the two glycoproteins, gp95$^{trk}$B and gp145$^{trkB}$(trkB), which are encoded by the trkB gene[24-26]. gp95$^{trk}$B is a truncated form of the trkB receptor molecule and lacks the tyrosine kinase domain[27]. NT-3 binds to gp$^{145trkC}$ (trkC) and also, with less affinity, to trkA and trkB[28]. The trkC gene locus also codes an isoform lacking the intracellular catalytic domain[28]. Additionally, all the NTs bind with low affinity to a transmembrane glycoprotein, p75$^{NGFR}$ (p75)[29]. The levels of trkA in the CNS are extremely low, and are concentrated to basal forebrain cholinergic neurons that are dependent on NGF[30]. Full-length trkB and trkC are expressed during the development of the CNS, and are down-regulated to barely detectable levels in the adult[31].

There is some evidence that neurons in the adult spinal cord and projection neurons to the spinal cord respond to BDNF and NT-3. BDNF and NT-3 treatment increased the number of regenerating axons 2-fold in Schwann cell seeded silicon tubes implanted into the midthoracic spinal cord[32]. Retrograde tracing showed that these neurons (92 per animal) were scattered throughout the rostral cord and into the brain stem. Schwab and colleagues showed that NT-3 enhances sprouting of corticospinal tract after lesion in the adult spinal cord. Rubrospinal projection neurons respond to BDNF following axotomy by upregulating GAP-43[33]. BDNF prevents neurotoxin-induced loss of 5-HT neurons and promotes sprouting of uninjured 5-HT axons[34]. Infusion of either BDNF or NT-3 significantly elevated the antinociceptive response in rat[35]. This response is mediated by descending 5-HT fibers.

There are changes in the expression of trkB following lesions in the spinal cord, however, only for transcripts of truncated trkB, which are increased throughout the scar in both rats and cats[36,37]. There is no change in either full-length trkB or trkC both in the scar and in the surrounding spinal cord tissue. The few axons which had regenerated into the scar were associated with the glial cells which express truncated trkB. Sciatic nerve or dorsal root lesions also upregulate truncated trkB in the spinal cord[38]. This upregulation in the scar or denervated tissue in the adult spinal cord could contribute to regeneration.

During the period of neurogenesis in the spinal cord of rat, both BDNF and NT-3 and their full-length catalytic receptors are upregulated[39-41]. Transcripts for both full-length trkB and trkC are expressed at low levels on embryonic day 13 (E-13) and progressively increase during the period of rapid neuronal growth and differentiation. Expression of trkB catalytic form in the CNS peaks on postnatal day 1 (P1) and progressively decreases to barely detectable levels in the adult; full-length trkC similarly peaks at P1 and decreases to levels comparable to E13 levels in the adult. Transcripts for the truncated trkB receptors also peak shortly after birth, and, by contrast, remain at relatively high levels in the adult. The level of p75$^{NGFR}$ transcripts is 5-fold higher at E13–14 than P1, and it also declines to barely detectable levels in the adult spinal cord. A similar pattern has been reported in developing spinal cord of chicks[39]. This developmental pattern of early expression of full-length trkB and trkC and significantly later expression of truncated trkB is common in wide variety of regions of the CNS and indicates that the regulation of the ratio of full-length to truncated NT receptors plays an important role in the development and maintenance of the CNS[39,40].

Consistent with this developmental pattern, neurons which regenerate or sprout following a lesion in the adult nervous system have upregulation of full-length trkB. Accompanying this upregulation is the upregulation of truncated receptors in glial cells associated with the neurite substrate.

The first example illustrating these changes is granule cell axons of the dentate gyrus; they sprout after seizures induced by intraventricular kainic acid injections or by electrolytic lesions in the hippocampus[42]. Full-length trkB mRNA and proteins are upregulated dramatically within 5 hours post-lesion over the cell bodies of granule cells. BDNF levels increase 30-fold, and NT-3 levels decreased over the same time course[42]. There are no changes in trkA or trkC mRNA expression.

Correlated with the above changes is the upregulation of GAP-43[43] which is a good marker for neurite outgrowth. Ischemic and hypoglycemic conditions result in similar changes in the hippocampus[44]. Further, mRNAs for BDNF and trkB are coexpressed in hippocampal neurons which suggests an autocrine mechanism[45]. Neurotrophins are also changed in the dentate gyrus following deafferentation (fornix-fimbria and perforant path lesions). Beck and colleagues[46] observed pronounced increase in truncated trkB over glial cells which match, in time and place, to the region into which sprouting of axons occurs. They speculate that "noncatalytic trkB molecules expressed on the surface of glial cells play an important role in plasticity of the adult brain, possibly regulating the concentration of bioactive neurotrophin or the responsiveness of neurotrophin receptors".

Another neuronal type in the adult nervous system which has upregulation of neurotrophin system following a lesion and during regeneration are neurons in dorsal root ganglia (DRG). BDNF as well as NGF are expressed in adult DRG neurons, and following sciatic nerve lesions, both are upregulated by 2- and 3-fold respectively[47]. Both full-length trkB and trkC levels are also increased (2 times and slightly, respectively), and p75 levels are transiently depressed and return to normal levels within 1 week[38,47]. Accompanying this is the upregulation of truncated trkB and trkC expression which is confined to Schwann cells[37,48]. These observations again suggest that the noncatalytic forms of the trkB and trkC as well as the p75$^{NGFR}$ might recruit or present the NT factors to the full-length receptors present on the regenerating axons[37,39,49]. The similarities between developing and regenerating neurons with respect to neurotrophic factors and their receptors suggest that these factors play a role in regeneration.

In summary, lesions in the spinal cord upregulate truncated forms of trkB in glial cells, but there are no changes in the full-length trkB associated with neurons. The presence of full-length trkB and trkC in most developing CNS neurons and in the neurons shown to regenerate in the adult nervous system (including the peripheral nervous system (PNS) led to the conclusion that upregulation of full-length catalytic trkB and trkC in neurons in the injured central nervous system will induce regeneration of axons and promote functional recovery.

An object of the present invention is to provide methods that result in survival and/or regeneration of neurons.

Another object of the present invention is to provide methods to induce expression of (upregulate) neurotrophic factor receptors trkB and trkC in neurons of the adult nervous system.

According to certain embodiments, the present invention provides methods for treating patients with nervous system damage, including but not limited to CNS trauma and strokes (e.g., spinal cord injury). According to certain embodiments the present invention provides methods for treating neurodegenerative disorders, including by not limited to, Alzheimer's disease, Parkinson's disease, Huntington's chorea, and amyotrophic lateral sclerosis and other motor neuropathies.

The present inventors have shown that treatment of adult spinal cord with the combination of all-trans retinoic acid (RA), dibutyryl cyclic AMP (dBcAMP) and KCl induces the expression of functional forms of trkB and trkC. The present inventors have also shown that such treatment is not damaging to the spinal cord and can be applied to treatment of neurotrauma, stroke, and neurodegenerative diseases. Without being limited to any theory of why such treatments work, the present inventors believe that the treatment results in upregulation of functional forms of trkB and trkC. Accordingly, the present methods can be used for conditions in which such upregulation is typically needed for functional recovery.

BRIEF DESCRIPTION OF THE FIGURES

FIG. 1. RNase protection analysis of BDNF and trkB mRNA expression in the PCC7 cells. Total RNA was isolated from control cells (0), cells treated one day with all-trans-RA (1R) and all-trans-RA plus dBcAMP (1RC), and cells treated three days with all-trans-RA (3R), dBcAMP (3C) or all-trans-RA plus dBcAMP (3RC). tRNA was used as a control for RNase protection.

DETAILED DESCRIPTION OF PREFERRED EMBODIMENTS

Figure 2:
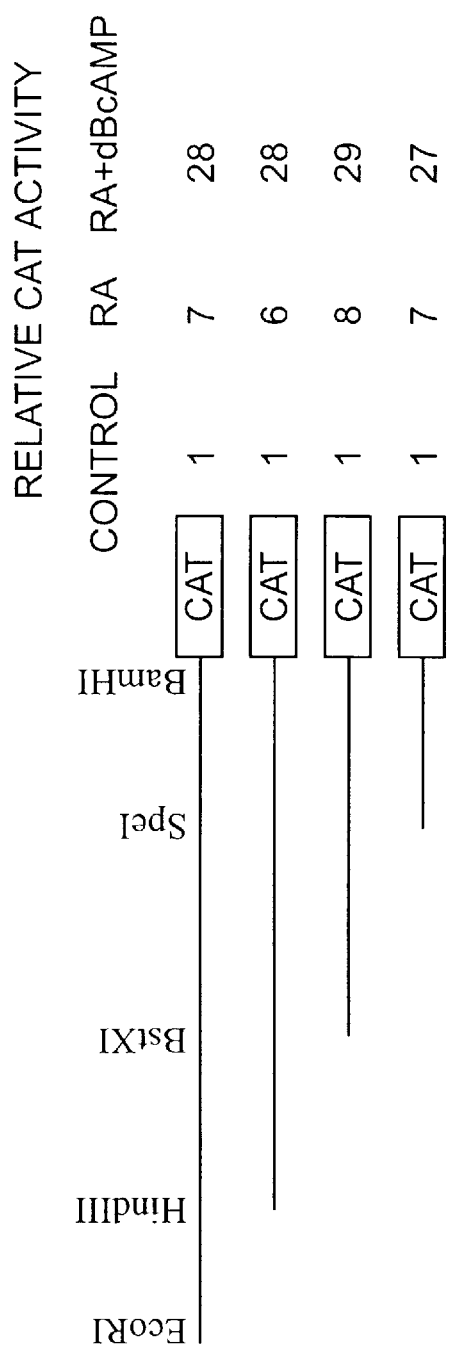
FIG. 2. Effect of all-trans-RA and dBcAMP on the TrkB promoter activity. PCC7 cells were transfected with TrkB promoter construct and CAT activity measured after treatment with all-trans-RA (RA) and dBcAMP.

The present invention is directed to methods of upregulation of the neurotrophic system. Such upregulation results in regeneration of neurons or in survival of neurons after trauma or stroke. The present inventors have particularly shown upregulation of trkB and trkC in the nervous system.

The inventors have shown that this upregulation can be achieved by activation of nuclear hormone receptors, such as the retinoic acid (RA) response system, activation of the second messenger response system, such as dibutyryl cyclic AMP (cAMP) response system, and elevation of $Ca^{2+}$. Several potential formulations can be used to activate these systems.

For example, retinoids, such as RA can be used to activate the nuclear hormone response system. The second messenger response system can be activated with, for example, cAMP, cyclic GMP, phosphinositols, phosphodiglycerols, tyrosine kinase, and ligands of jak/stat ligand kinase system. According to certain preferred embodiments, calcium channel stimulators, such as potassium chloride (KCl) can be used to elevate $Ca^{2+}$.

The inventors have specifically shown upregulation of both trkB and trkC in both in vitro and in vivo conditions with all-trans-RA, dBcAMP, and KCl. Since activation of trkB and trkC systems have been shown to promote neuronal growth and survival, this invention can be used for treatment of CNS stroke and trauma, as well as for treatment of neurodegenerative diseases, for example, Parkinson's, Alzheimer's, Huntington's chorea, and amyotrophic lateral sclerosis.

For CNS trauma and stroke patients, this combination treatment can be applied to neurons in the area of the lesion to promote regeneration. In Alzheimer's disease, upregulation of trkB and trkC can be used to slow or prevent the loss of forebrain cholinergic neurons which is believed to be in part responsible for clinical signs of the disease. In Parkinson's patients, the upregulation of trkB and trkC can be used to slow or arrest the loss of dopamine neurons and also to elevate dopamine metabolism in the remaining neurons. Both effects could increase the available stores of dopamine neurotransmitter and eliminate or reduce the need for L-DOPA drug therapy, which has negative side effects. In amytrophic lateral sclerosis patients, upregulation of trkB and trkC can be induced in pools of motor neurons to slow or prevent the spontaneous loss of these neurons. Accompanying this RA, cAMP, and KCl treatment to upregulate the trkB and trkC receptors in all of the above clinical conditions, the neurotrophic factors which activate these receptors, BDNF and NT-3, can be concurrently given to further activate this neurotrophic system.

One skilled in the art will be able to optimize treatment parameters (e.g., dosage or delivery of the treatment) using human cells in culture, animal tests, and clinical work in humans. Moreover, the patients to be treated can be human or other animals.

According to certain embodiments, the claimed invention can be used to treat patients suffering from trauma or stroke. The treatment can be used to increase the survival of neurons after trauma or stroke and/or to regenerate neurons. Accordingly, the treatment can improve the condition of patients or prevent patients from suffering from worsening of conditions. For example, functions that may be lost in normal untreated trauma or stroke patients may be improved, restored, or prevented from being lost. Also, the present invention may be used in conjunction with other treatments that address other aspects of potential recovery from or prevention of neuronal damage.

RA stimulates growth and survival of spinal cord neurons, induces differentiation of neuronal cell lines, and induces expression of neurotrophic factors and their receptors in different neuronal cells. Initially, the present inventors performed the analyses in vitro using cell cultures in order to understand mechanisms of induction. This in vitro work provided the present inventors with treatment parameters for inducing the neurotrophic factor system in the adult spinal cord.

The following examples illustrate aspects of the invention. These examples are for illustrative purposes only and are not intended to limit the scope of the invention.

EXAMPLE 1.
Induction of expression of trkB in vitro

The present inventors screened several teratocarcinoma and neuroblastoma cell lines including mouse teratocarcinomas P19, PCC7, F9, and mouse neuroblastomas N18 and Neuro2A for the inducibility of the trkB gene to find a good model system for the BDNF and trkB expression analyses. RNase protection analyses using 0.39 kb HincII/ScaI fragment covering partially transmembrane and kinase domain were performed to obtain expression of truncated and full-length forms of trkB. Total RNA (25 micrograms per analyses) isolated from the above-listed cell lines and "Ambion RNase protection kit RPA II" were used in these experiments. The instructions provided in that kit was followed to perform this work.

The screening revealed that the trkB gene is induced in teratocarcinoma PCC7 cells after treatment with all-trans-RA at a concentration of $10^{-7}$ M for three days (FIG. 1). (All-trans-RA was added into the growth media (DMEM+ 10% fetal calf serum)). Moreover, the RNase protection assay demonstrated that undifferentiated PCC7 cells express only truncated form of trkB and that all-trans-RA treatment induces the expression of full length form of trkB (FIG. 1). The same treatment with all-trans-RA also induces BDNF mRNA expression in PCC7 cells (FIG. 1).

These preliminary data suggest that induction of the full-length form of trkB in the PCC7 cells may contribute to the neuronal differentiation of these cells after treatment with all-trans-RA. It has been demonstrated that all-trans-RA induces full length trkB which results in neuronal differentiation in several neuroblastoma cell lines[50].

EXAMPLE 2.
Induction of trkB promoter—in vitro analysis

RA has been shown to regulate expression of several neurotrophic factors and their receptors[50]. The present inventors analyzed the effect of RA and dibutyryl cyclic AMP (cAMP) on the activity of trkB promoter using bacterial chloramphenicol acetyltransferase (CAT) gene as a heterologous reporter gene.

A mouse genomic library (Stratagene) derived from liver DNA of Balbc adult mice was screened with 1.8 kb 5' cDNA fragment (mouse TrkB cDNA was from M. Metsis, Karolinska Institut, Sweden) at high stringency conditions (0.1× SSC, 65° C.) to isolate the 5' regulatory region of the trkB gene. One of the isolated phages was found to contain a 19 kb insert that included 400 bp of the cDNA 5' fragment and an additional 18.6 kb of 5' flanking DNA region of the trkB gene.

Several deletion constructs of the trkB 5' regulatory region in the front of CAT reporter gene were tested for their inducibility with RA in teratocarcinoma PCC7 cells. Deletion constructs were generated by digestion of the above-noted phage DNA with appropriate enzymes. Specifically, the phage DNA was separately digested with EcoRI, HIndIII, BstXI, and BamHI. The fragments generated were then cloned into the CAT3N reporter plasmid.

These expression constructs were then separately transfected into PCC7 cells and the cells were treated with all-trans-RA ($10^{-7}$ M) or with all-trans-RA ($10^{-7}$ M) plus dibutyryl cAMP (1 mM). Either all-trans-RA ($10^{-7}$ M) or all-trans-RA ($10^{-7}$ M) plus dibutyryl cAMP (1 mM) were added directly to the growth media (DMEM+10% fetal calf serum).

All the deletion constructs (−7 kb EcoRI, −5 kb HindIII, −3.5 kb BstXI, and −2 kb BamHI) were inducible with all-trans-RA and all-trans-RA plus dcAMP; RA alone induced activity about 7 fold, and RA plus dBcAMP induced activity about 30 fold (FIG. 2). Sequence analyses of the 800 bp 5' regulatory region reveals several binding sites for nuclear hormone receptors.

Since the sequence analyses of the promoter region of several neurotrophic factors and neurotrophic factor receptors revealed a presence of response elements for RA, cAMP, and serum response element (sequence CCATATTAGG), the present inventors analyzed the effect of RA, dBcAMP, and elevated levels of $Ca^{2+}$ on the trkB promoter activities in primary cortical neuronal cultures and PCC7 cells using the transient CAT assay. Neuronal cells from mouse embryonic day 15–17 cerebral cortexes were cultured in Neurobasal medium (Gibco) with B27-supplement (Gibco). CAT3N reporter plasmids containing trkB promoter CAT construct were transfected into cortical neurons and PCC7 cells and CAT activities were analyzed 48 hours after treatment with all-trans-RA ($10^{-7}$ M), dibutyryl cAMP (1 mM), and KCl (50 mM). All-trans-RA, dibutryryl cAMP, and KCl were added directly into the culture media.

Figure 3:
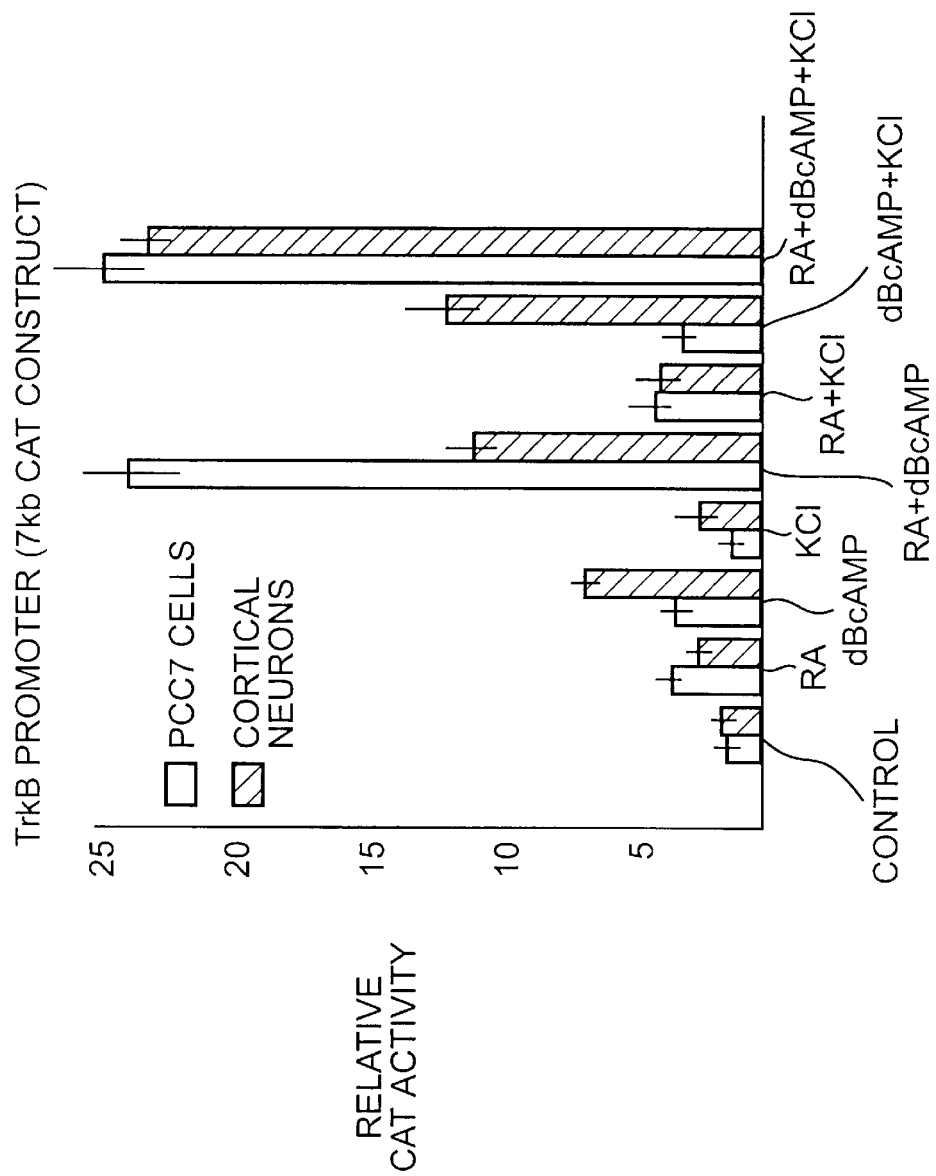
FIG. 3. Induction of TrkB promoter activity in mouse cortical neurons and PCC7 cells.

To elevate intracellular $Ca^{2+}$ levels, we treated the cells with KCl. In both primary cortical neuronal cultures and PCC7 cells, KCl alone does not stimulate BDNF and trkB promoters significantly (FIG. 3). Also, treatment with KCl plus all-trans-RA or KCl plus dBcAMP did not change trkB promoter activity in PCC7 cells, but KCl plus dBcAMP treatment resulted in significant increase in promoter activity in cortical neurons (FIG. 3).

Treatment with all-trans-RA and dBcAMP results in about 25 times stimulation of BDNF promoter activity and trkB promoter activity in PCC7 cells and about 12 times stimulation of trkB promoter activity in cortical neurons. These data indicate that the combination of RA, dBcAMP, and KCl is responsible for the induction of trkB gene.

EXAMPLE 3.
Inducibility of trkB and trkC in the adult nervous system

The present inventors analyzed the expression of trkB and trkC in adult normal and injured spinal cord after treatment of animals with combinations of all-trans-RA ($10^{-5}$ M), dibutyryl cAMP (2 mM), or KCl (50 mM) in PBS. Intraspinal cannulae were implanted to the spinal cord and connected to subcutaneous osmotic pumps (ALZET model 2ML2) with infusion rates of 5 µl/hr for 14 days. As a control, PBS was used. After treatment, animals were sacrificed and 1 cm fragments of spinal cord were isolated and used for RNA extraction. Three animals per treatment group were analyzed. RNase protection analyses using 0.39 kb HincII/ScaI fragment covering partially transmembrane and kinase domain of trkB and polymerase chain reaction (PCR) amplified 297 bp transmembrane region of trkC RNA probes were performed to obtain expression of trkB and trkC mRNA. Total RNA (5 micrograms per analyses) isolated from control and treated spinal cords and "Ambion RNase protection kit RPA II" were used in these experiments. Radioactivity in protected fragments were measured and quantified using Phosphorimager analysis (Molecular Dynamics).

Expression of trkB and trkC in spinal cord were not changed after RA or RA plus dibutyryl cAMP treatments 8 hours post-treatment. Sequence analysis of trkB gene promoter region revealed regulatory elements which are known to mediate $Ca^{2+}$ effects. It has been also demonstrated that depolarization using KCl induces neurotrophic factor gene expression[54]. Also, stimulation of excitatory amino acid receptors induce expression of neurotrophins in certain CNS neuronal populations, but not in the spinal cord[48, 51].

Figure 4:
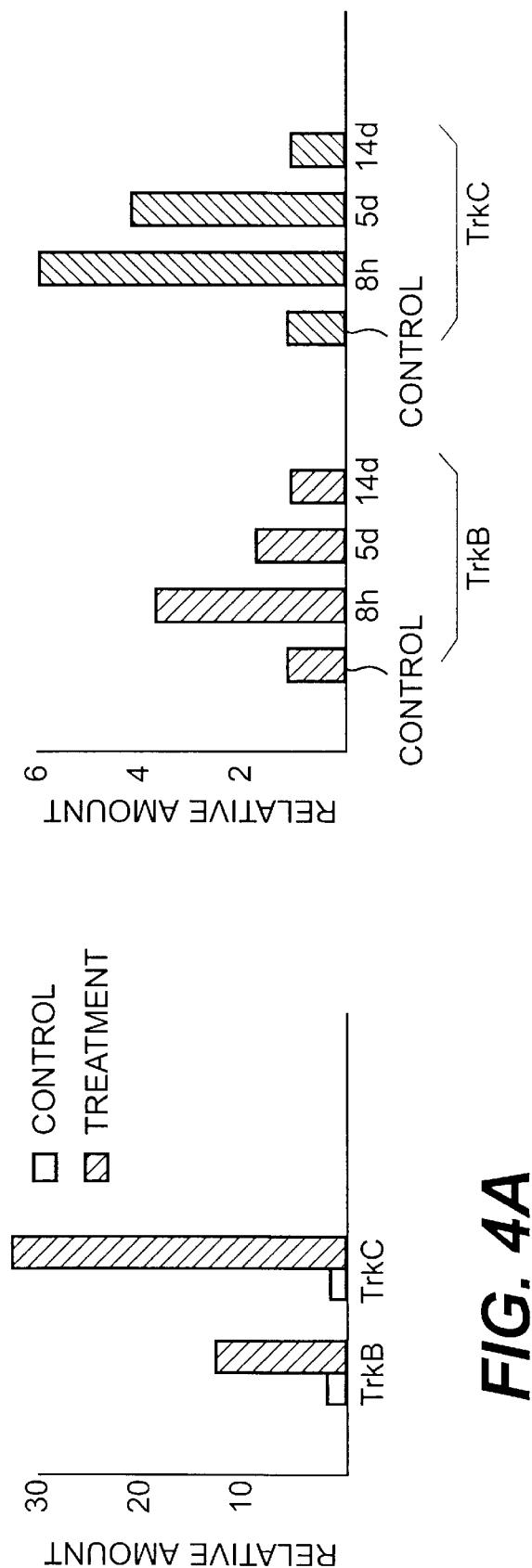
FIG. 4. Quantitative analyses of RNase protection analysis data of induction of TrkB and TrkC full length forms in the spinal cord. (A) Total RNA was isolated from control and treated with RA+dBcAMP+KCl for 8 hours. (B) Total RNA was isolated from control and treated with RA+dBcAMP+KCl for 8 hours, 5 days, or 14 days.

Initially the present inventors treated uninjured rates with RA ($10^{-5}$ M), dBcAMP (2 mM), and KCl (50 mM) for 8 hours and analyzed expression of trkB and trkC expression at the site of the cannulation. This treatment resulted in a 12 fold induction of trkB full length form whereas the level of truncated form remained essentially unchanged (FIG. 4A). Expression of trkC was induced about 34 fold (FIG. 4A). Next, the present inventors analyzed induction of trkB and trkC in chronically injured spinal cord after combined treatment with RA, dibutyryl cAMP, and KCl for 8 hours, 5 and 14 days. A contusion injury was made by dropping a 10 gm weight a distance of 2.5 cm onto the dorsal surface of thoracic level 9 of the spinal cord. The upregulation of both trkB and trkC mRNA peaked at 8 hours (4× and 6×, respectively), remained slightly above control levels at 5 days, and returned to control levels by 14 days.

These results indicate that it is possible to induce expression of neurotrophic factor receptors in the adult spinal cord. In the next example we determined if this treatment restores function in chronically injured spinal rats.

EXAMPLE 4.
Effect of combined treatment of RA, dBcAMP and KCl on locomotor function in rats with chronically injured spinal cords With the finding that the combination treatment of RA, dBcAMP, and KCl upregulated full-length trkB and trkC in the adult spinal cord, the present inventors conducted an experiment on rats with chronically injured spinal cords. The present inventors tested whether this treatment improves or further impairs locomotor behavior. The animals were given intraspinal infusions of this 3-substance treatment 9 weeks post-injury. Behavioral testing was done 2, 3, 4, and 6 weeks post-treatment.

Twenty adult female rats were subjected to a contusion injury of a 10 g weight dropped 2.5 cm onto level T-9, and five animals (uninjured controls) were prepared similarly with the exception of not being impounded with the weight. Post-operatively, the animals were tested weekly for the pattern of behavioral recovery using the Wrathall and colleagues Combined Behavioral Score (CBS) battery of tests[55]. The test analyzed hindlimb coordination and reflexes. The reflexes tested included toe-spread, placing, withdrawal in response to extension, pressure or brief pain, righting and the reflex to lick the toes in response to heat. Coordinated motor activity was observed in an open field test (modification of the Tarlov[56]), while swimming, and on an inclined plane. The results of the individual tests were combined to derive the CBS score. This converted score assigns points for abnormalities in functions; the maximum deficit is 100% and a normal animal has the CBS of 0%.

Nine weeks post-injury, intraspinal cannulae were implanted one segment rostral to the injury site and connected to subcutaneous osmotic pumps (ALZET model 2ML2) with infusion rates of 5 µl/hr for 14 days. Nine injured animals (treatment group) received pumps which delivered the combination of all-trans-RA ($10^{-5}$ M), dBcAMP (2 mM), and KCl (50 mM) in PBS, and the remaining injured animals had pumps which delivered PBS (PBS controls). Two animals died prior to treatment. Pretreatment behavioral tests of functional deficits were performed 7, 8 and 9 weeks post-injury.

Figure 5:
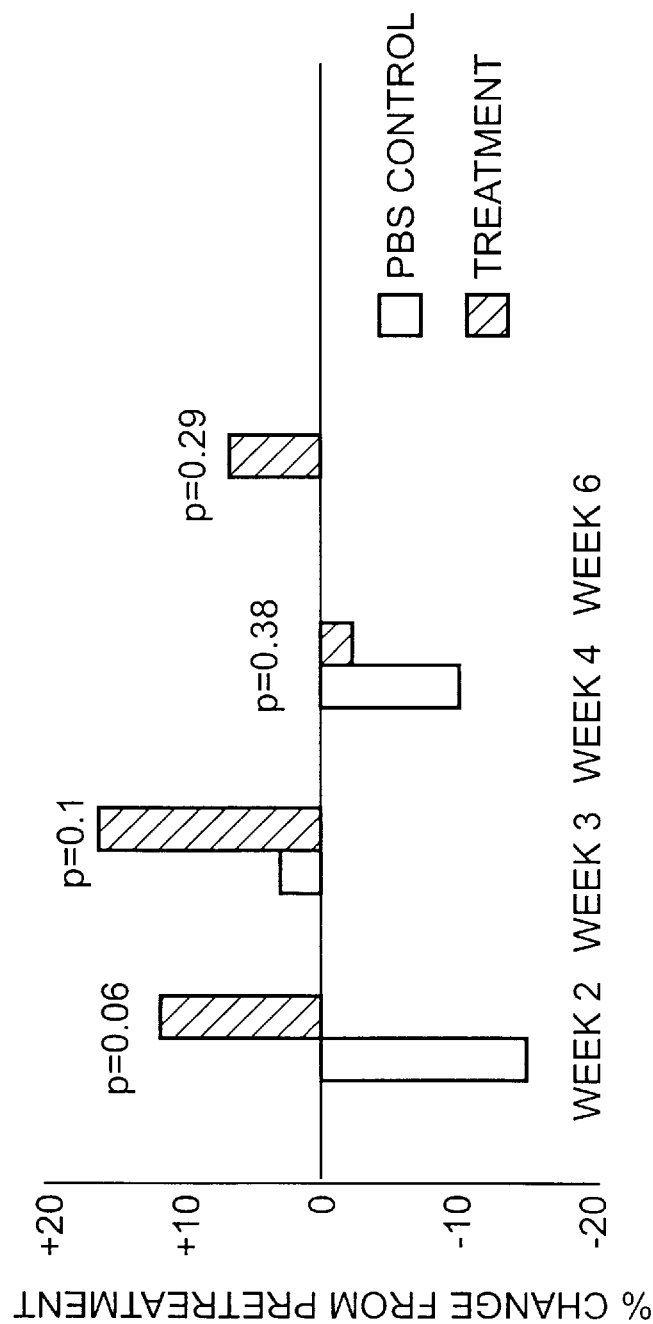
FIG. 5. Changes in behavior (CBS) of chronically injured spinal rats following treatment with RA, dBcAMP, and KCl.

None of the groups reached statistical differences beyond p-value 0.05 using the t-test of variability. There was, however, a positive trend for improvement two and three weeks post-treatment (FIG. 5). Two weeks post-treatment, the CBS of the treated animals showed 12% less deficit compared to the pretreatment CBS; the PBS control group showed a 15% greater deficit over the same time period. Three weeks post-treatment, the treatment group maintained the same improvement (16% change from pretreatment CBS) and the PBS control group showed a 3% improvement in CBS. The CBSs between the two groups showed no differences at 4 and 6 weeks post-treatment. This transient trend in improvement after 2 and 3 weeks of treatment is encouraging and there is also no evidence that the treatment causes further damage.

EXAMPLE 5.
Analysis of regeneration of descending serotonergic fibers

To determine whether this treatment of RA, dBcAMP, and KCl promotes regeneration of axonal processes, the present inventors analyzed the number of serotonergic fibers at different levels caudal to the site of injury. The serotonergic fibers are from cell bodies rostrad to the site of injury so the number of serotonergic fibers caudad to the site of lesion represents a good index of the amount of regeneration of axons which has occurred across the site of lesion.

After finishing the locomotor analyses (Example 4), the animals were perfused with 4% paraformaldehyde in phosphate buffer. Three segments of the spinal cord were collected for analyses of descending serotonergic fibers 5, 15, and 25 mm caudad from the epicenter of the injury site. The tissue was frozen on a block of dry ice and stored at −70° C.

For analysis of 5-HT fibers, the three caudal segments of cord for each animal were mounted on the same cryostat chuck so transverse sections of the spinal cord were obtained at 5, 15, and 25 mm caudad from the epicenter of the injury site. Four to five slides were prepared for each animal and processed for 5-HT immunocytochemistry. The sections of tissue were initially washed three times in PBS, placed in 0.3% Triton X-100/10 normal goat serum in 0.01 M PBS for 15 minutes, and incubated overnight at 4° C. in the primary antibody in 0.01% bovine serum albumin/phosphate buffered saline (BSA/PBS). The primary antibody was visualized using Vectastain ABC kit (Vector Laboratories) and 3,3'-diaminobenzidine tetrahydrochloride as a substrate for horseradish peroxidase.

Figure 6:
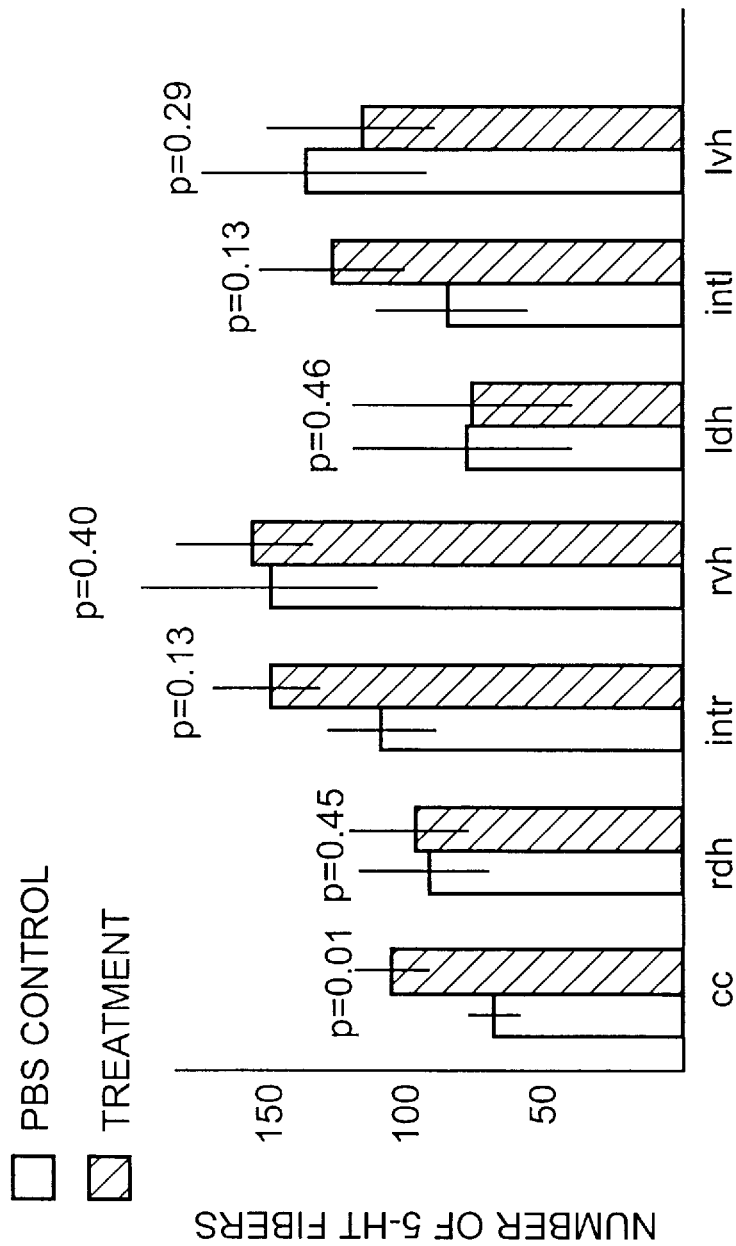
FIG. 6. Changes in 5-HT immunoreactive fibers distal (15 mm) to the lesion site in chronically injured spinal rats 7 weeks post-treatment of RA, dBcAMP, and KCl.

NIH Image software was used to count the number of 5-HT immunoreactive fibers. For each transverse plane, counts of 5-HT immunoreactive fibers were made bilaterally in dorsal horn (dhl and dhr), intermediate gray (intl and intr), and ventral horn (vhl and vhr) and in the region around the central canal (cc). The software was programmed to only count cross sections of immunoreactive images. In the plane 15 mm caudad to the injury site, there was a significant increase of 5-HT immunoreactive fibers in the region around the central canal (cc) (FIG. 6). None of the other regions showed any significant difference.

EXAMPLE 6.

Therapeutic Applications

The upregulation of neurotrophic systems can be used in the treatment of patients with nervous system damage including but not limited to CNS trauma and strokes (e.g. spinal cord injury) and to neurodegenerative disorders including but not limited to Alzheimer's, Parkinson's, Huntington's chorea, amyotrophic lateral sclerosis, and other motor neuropathies.

(A)

In treatment of spinal cord injury, there are two ways in which the presently claimed treatment can contribute to recovery of function. First, both retrograde and anterograde death of neurons occurs following injury[57,58], and treatment with neurotrophic factors has been shown to rescue neurons[14–16]. Secondly, treatment with BDNF and NT-3 has been shown to activate axon growth from neurons which project axons to the spinal cord[32–35]. Also, trkB and trkC receptors are expressed during the development of spinal cord neurons and are down regulated to barely detectable levels in the adult spinal cord and brain[31].

According to certain embodiments, the combination treatment of all-trans-RA, cAMP, and KCl can be administered both rostrad and caudad to the site of injury to upregulate the receptors for trkB and trkC. Also, the neurotrophic factors (BDNF and NT-3), which activate these receptors, can be given concurrently to optimize activation of this system. Optimal treatment parameters can be developed using human cells in vitro, and also by in vivo work in animals including humans.

(B)

Another therapeutic example is to upregulation of trkB and trkC receptors in the treatment of Alzheimer's disease. The loss of cholinergic function in the septohippocampal and basalocortical projection is believed to be in part responsible for behavioral deficits characterizing the disease[59,60]. Treatment with BDNF has been shown to rescue these cholinergic neurons from degenerative changes following damage[15,16].

According to certain embodiments, this loss of forebrain cholinergic neurons can be arrested or slowed by the upregulation of the BDNF response. The combination of all-trans RA, cAMP, and KCl can be delivered to these cholinergic neurons to upregulate the trkB receptors; additionally, BDNF can be given simultaneously to optimize activation of the upregulated of the receptors. Optimal treatment parameters can be developed using human cells in vitro, and also by in vivo work in animals.

(C)

Another therapeutic example is to upregulate the neurotrophic systems in the treatment of Parkinson's disease. Parkinsonism is a slowly progressing disease, and it is believed that the loss of brain stem dopamine neurons is responsible for the behavioral deficits. These neurons are located in the substantia nigra nucleus of the brain stem and project to and terminate in the basal ganglia. Chronic infusions of BDNF to the substantia nigra neurons elevates dopamine metabolism[61].

According to certain embodiments, the combination treatment of all-trans-RA, cAMP, and KCl can be infused to the substantia nigra nucleus to upregulate trkB receptors, and again BDNF can be given to optimize activation of this neurotrophic system. This treatment should elevate dopamine metabolism and increase dopamine release in the basal ganglia to alleviate the Parkinson's symptoms. Optimal treatment parameters can be developed using human cells in vitro, and also by in vivo work in animals.

(D)

Another therapeutic example is to treat motoneuron neuropathies including amyotrophic lateral sclerosis by upregulating the trkB and trkC system in motor neurons in the spinal cord and brain stem. In this disease, the behavioral deficits are caused by the spontaneous loss of motor neurons. Treatment with BDNF has been shown to rescue motoneurons following axotomy[14] and also to arrest the motor deficits in a genetic disease in which motor neurons spontaneously die[62] ("wobbler" genetic mutant in mice).

According to certain embodiments, the combination treatment of all-trans-RA, cAMP, and KCl can be made into the motor columns of the spinal cord or brain stem to upregulate trkB. BDNF and NT-3 can be given simultaneously to optimize activation of the system. Optimal treatment parameters can be developed using human cells in vitro, and also by in vivo work in animals.

(E)

The delivery system for infusing the combination treatment of all-trans retinoic acid, cAMP, and KCl to neurons in the CNS involves implanting an intraparenchymal cannula to the appropriate pool of neurons, and the cannula is attached to an osmotic pump. Detailed descriptions for surgically implanting cannula and its effectiveness for spinal cord treatment is described in Example 4 above. This same delivery system can be used for treatment to any part of the CNS and PNS. Also the three components are not limited to all-trans RA, cAMP, and KCl. This disclosure includes other components that activate a nuclear hormone receptor, that activate the second messenger response system, and that elevate $Ca^{2+}$.

It will be apparent to those skilled in the art that various modifications and variations can be made in the processes and products of the present invention. Thus, it is intended that the present invention cover the modifications and variations of this invention provided they come within the scope of the appended claims and their equivalents.

BIBLIOGRAPHY:

1. Ramon y Cajal S, 1928, Degeneration and Regeneration of the Nervous System, Oxford University Press, translated by R M May.

2. Reier P, B S Bregman, J R Wujek, and A Tessler. 1986. Intraspinal transplantation of fetal spinal cord tissue: An approach toward functional repair of the injured spinal cord, In: "Development and Plasticity of the Mammalian Spinal Cord,") M E Goldberger, A Sorio and M Murray, eds, Liviana Press, Padova.

3. Richardson P M, McGuinness U M, Aguayo A J. 1982. Peripheral nerve autografts to the rat spinal cord: studies with axonal tracing methods. Brain Res 237:147–162.

4. Guth L, C P Barret, E J Donati, F D) Anderson, M V Smith, and M Lifson. 1985. Essentiality of a specific cellular terrain for growth of axons into the spinal cord lesion. Exp Neurol. 88:1–12.

5. Nornes H, S J Moorman, A R Mihajlov, B E Pulford, and L R Whalen. 1993. Intraspinal transplants of catecholamine containing cells and fetal spinal cord and iris tissues in the adult rat. In: "Advances in Neurology, Neuronal Injury and Regeneration". Vol. 59: 185–197. Ed. F J Seil, Raven Press, N.Y.

6. Houle, J D. 1991. Demonstration of the potential for chronically injured neurons to regenerate axons into intraspinal peripheral nerve grafts. Exp Neurol 113; 1–9.

7. Richardson P M, V M McGuinness, A J Aguayo. 1980, Axons from CNS neurons regenerate into PNS grafts. Nature, 284:264–265.

8. David D S, A J Aguayo. 1981. Axonal elongation into PNS "bridges" after central nervous system injury in adult rats. Science 214:931–933.

9. Schnell L, R Schneider, R Kolbeck, Y A Barde, M E Schwab. 1994. Neurotophin-3 enhances sprouting of corticospinal tract during development and after adult spinal cord lesion. Nature, 367:170–173.

10. Xu X M, V Guenard, N Kleitman, and M B Bunge. 1995. Axonal regeneration into Schwann cell-seeded guidance channels grafted into transected adult rat spinal cord. J Comp Neur, 145:145–160.

11. Maness L M, A J Kastin, J T Weber, W A Banks, B S Beckman and J E Zadina. 1994. The neurotrophins and their receptors: structure, function, and neuropathology. Neurosc and Biobehav Rev. 18:143–159.

12. Klein R. 1994. Role of neurotrophins in mouse neuronal development. FASEB J. 8:738–744.

13. Ip N Y, and G D Yancopoulos. 1994. Neurotrophic factors and their receptors. Ann Neurol. 35:S13–S15.

14. Yan Q, J Elliott and W D Snider. 1992. Brain-derived neurotrophic factor rescues spinal motor neurons from axotomy-induced cell death. Nature. 360:753–755.

15. Knusel B, L D Beck, J W Winslow, A Rosenthal, L E Burton, H R Widmer, K Nikolics, and F Hefti. 1992. Brain-derived neurotrohic factor administration protects basal forebrain cholinergic but not nigral dopaminergic neurons from degenerative changes after axotomy in the adult rat brain. J of Neuro. 12:4391–4402.

16. Morse I D, S J Wiegand, K Anderson, Y You, N Cai, J Carnahan, J Miller, P S DiStefano, C A Altar, R M Lindsay, and R F Alderson. 1993. Brain-derived neurotrophic factor (BDNF) prevents the degeneration of medial septal cholinergic neurons following fimbria transection. J of Neur. 13:4146–4156.

17. Levi-Montalcini R, V Hamburger. 1953. A diffusible agent of mouse sarcoma producing hyperplasia of sympathetic ganglia and hyperneurotization of viscera in the chick embryo. J Exp Zool 123:233–288.

18. Barde Y A, D Edgar, and H Thoenen. 1982, Purification of a new neurotrophic factor from mammalian brain. EMBO J, :549–553.

19. Maisonpierre P C, L Belluscio, S Squinto, N Y Ip, M E Furth, R M Lindsay, G D Yancopoulos. 1990. Neurotrophin-3: A neurotrophic factor related to NGF and BDNF. Science 247:1446–1451.

20. Hohn A, J Leibrock, K Bailey, and Y A Barde. 1990. Identification and characterization of a novel member of the nerve growth factor-brain-derived neurotrophic factor family. Nature 344:339–341.

21 Hallbook F, C F Ibanez and H Persson. 1991. Evolutionary studies of the nerve growth factor family reveal a novel member abundantly expressed in Xenopus ovary. Neuron 6:845–858.

22. Klein R, S Jing, V Nanduri, E O'Rourke, M Barbacid. 1991. The trk protooncogene encodes a receptor for nerve growth factor. Cell 65:189–197.

23. Kaplan D R, D Martin-Zanca, L F Parada. 1991. Tyrosine phosphorylation and tyrosine kinase activity of the trk proto-oncogene product induced by NGF. Nature 350:158–160.

24. Klein R, V Nanduri, S Jing, F Lamballe, P Tapley, S Bryant, C Cordon-Cardo, K R Jones, L F Reichardt, and M Barbacid. 1991. The trkB tyrosine protein kinase is a receptor for brain- derived neurotrophic factor and neurotrophin-3. Cell 66:395–402.

25. Soppet D, E. Escandon, J Maragos, D S Middlemas, S W Reid, J Blair, L E Burton, B R Stanton, D R Kaplan, T Hunter, D Nikolics, and L F Parada. 1991. The neurotrophic factors brain-derived neurotrophic factor and neurotrophin-3 are ligands for the trkB tyrosine kinase receptor. Cell 65:895–903.

26. Squinto S P, T N Stitt, T H Aldrich, S Davis, S M Bianco, C Radziejewski, D J Glass P Masiakowski, M E Firth, D M Valzuela, P S DiStefano, and G. D. Yancopoulos. 1991. trkB encodes a functional receptor for brain-derived neurotrophic factor and neurotophin-3 but not nerve growth factor. Cell 65:885–893.

27. Middlemas D S, R A Lindberg, T Hunter. 1991. trkB, a neural receptor protein-tyrosine kinase: evidence for a full-length and two truncated receptors. Mol Cell Biol 11:143–153.

28. Lamballe F, R Klein, and M Barbacid. 1991. TRK-C, a new member of the TRK family of tyrosine protein kinases, is a receptor for neurotrophin-3. Cell 66:967–979.

29. Sutter A, R I Riopelle, R M Harris-Warrick and E M Shooter. 1979 Nerve growth factor receptors:

characterization of two distinct classes of binding sites on chick embryo sensory ganglia cells. J Biol Chem 254:5972–5982.

30. Merlio J P, P Ernfors, M Jaber and H Persson. 1992. Molecular cloning of rat trkC and distribution of cells expressing messenger RNAs for members of the trk family in the rat central nervous system. Neurosc 51:513–532.

31. Escandon E, D Soppet, A Rosenthal, J L Mendoza-Ramirez, E Szonyi, L E Burton, C E Henderson L F Parada and K Nikolics. Regulation of neurotophin receptor expression during embryonic and postnatal development. J of Neurosc 14:2054–2068.

32. Xu X M, V Guenard, N Kleittnan, and M B Bunge. 1994. BDNF and NT-3 promote axonal regeneration of brainstem neurons into Schwann cell grafts in mid-thoracic spinal cord of adult rats. Soc for Neurosci 20: 1111.

33. Kobayashi N R, A Bedard and W Tetzlaff. 1994. Stimulation of GAP-43 and T$\alpha$1 -Tubulin mRNA expression by BDNF in rat rubrospinal neurons after thoracic axotomy. Soc for Neuro 20:697.

34. Mamounas L, M E Blue, J A Siuciak and C Anthony. 1994. BDNF prevents the neurotoxin-induced loss of 5-HT axons and promotes sprouting of uninjured 5-HT axons in rat brain. Soc for Neuro 20:441.

35. Siuciak J A, C A Altar, S J Wiegand and R M Lindsay. 1994. Antinociceptive effect of brain-derived neurotrophic factor and neurotrophin-3. Brain Res 633:326–330.

36. J Frisen, V M K Verge, S Cullheim, H Persson, K Fried, D S Middlemas, T Hunter, T Hokfelt, and M Risling. 1992. Increased levels of trkB MRNA and trkB protein-like immunoreactivity in the injured rat and cat spinal cord. Proc Natl Acad Sci 89:11282–11286.

37. Frisen J, M Valerie, K Verge, K Fried, M Risling, H Persson, J Trotter, T Hokfel and D Lindholm. 1993. Characterization of glial trkB receptors: Differential response to injury in the central and peripheral nervous systems. Proc Natl Acad Sci 90:4971–4975.

38. Ernfors P, C M Rosario, W Merlio, G Grant, H Aldskogius and H Persson. 1993. Expression of mRNAs for neurotrophin receptors in the dorsal root ganglion and spinal cord during development and following peripheral or central axotomy. Mol Brain Res 17:217–226.

39. Escandon E, D Soppet, A Rosenthal, J Mendoza-Ramirez, E Szonyi, L E Burton C E Henderson, L F Parada and K Nikolics. 1994. Regulation of neurotrophin receptor expression during embryonic and postnatal development. J of Neurosc 14:2054–2068.

40. Ernfors P, J P Merleo and H Persson. 1992. Cells expressing mRNA for neurotrophins and their receptors during embryonic rat development. Eur J of Neurosc 4:1140–1158.

41. Klein R, D Martin-Zanca, M Barbacid and L F Parada 1990. Expression of the tyrosine kinase receptor gene trkB is confined to the murine embryonic and adult nervous system. Develop 109:845–850.

42. Rocamora N, J M Palacios and G Mengod. 1992. Limbic seizures induce a differential regulation of the expression of nerve growth factor, brain-derived neurotrophic factor and neurotrophin-3, in the rat hippocampus. Mol Brain Res 13:27–33.

43. Meberg P J, C M Gall and A Routtenberg. 1993. Induction of F1/GAP-43 gene expression in hippocampal granule cells after seizures. Mol Brain res 17:295–297.

44. Merlio J P, P Ernfors, Z Kokaia, D S Middlemas, J Bengzon, Merab Kokaia, M Smith, B K Siesjo, T Hunter, O Lindvall, and H Persson. 1993. Increased production of the trkB protein tyrosine kinase receptor after brain insults. Neuron 10:151–164.

45. Kokaia Z, J Bengzon, M Metsis, M Kokaia, H Persson, and O Lindvall. 1993. Coexpression of neurotrophins and their receptors in neurons of the central nervous system. Proc Natl Acad Sci 90:6711–6715.

46. Beck K D, F Lamballe, R Klein, M Barbacid, P E Schauwecker, T H McNeill, C E Finch, R Hefti, and J R Day. 1993. Induction of noncatalytic TrkB neurotrophin receptors during axonal sprouting in the adult hippocampus. J of Neurosc 13:4001–4–14.

47. Sebert M E, E M Shooter. 1993. Expression of mRNA for neurotrophic factors and their receptors in the rat dorsal root ganglion and sciatic nerve following nerve injury. J of Neurosc Res 36:357–376.

48. Funakoshi H, J Frisen, G Barbany, T Timmusk, O Zachrisson, V M K Verge and H Persson. 1993. Differential expression of mRNAs for neurotophins and their receptors after axotomy of the sciatic nerve. J of Cell Biol 123:455–465.

49. Ghosh A, J Carnahan, M E Greenberg. 1994. Requirements for BDNF in activity-dependent survival of cortical neurons. Science 263: 1618–1621.

50. Kaplan D R, K Matsumoto, E Lucarelli, C J Thiele. 1993. Induction of trkB by retinoic acid mediates biologic responsiveness to BDNF and differentiation of human neuroblastoma cells. Neuron 11:321–331.

51. Timmusk T, K Palm, M Metsis, T Reintam, V Paalme, M Saarma and H Persson. 1993. Multiple promoters direct tissue-specific expression of the rat BDNF gene. Neuron 10:475–489.

52. Pfeiffer, S., H. Jakob, K. Mikoshiba, P. Dubois, J. Guenet, J. Nicolas, J. Gaillard, G. Chevance and F. Jacob. 1981. Differentiation of a teratocarconoma cell line: preferential development of cholinergic neurons. J. Cell Biol. 88:57–66.

53. Wrathall J R, R K Pettegrew, F Harvey. 1985. Spinal cord contusion in the rat: Production of graded, reproducible, injury groups. Ex Neur 88:1 08–122.

54. Ghosh A, M E Greenberg. 1995. Calcium signaling in neurons: molecular mechanisms and cellular consequences. Science 268: 239–247

55. Gale K, H Kerasidis, J R Wrathall. 1985. Spinal cord contusion in the rat: Behavioral analysis of functional neurologic impairment. Exp Neur 88:123–134.

56. Tarlov I M, H Klinger. 1954. Spinal cord compression studies. II. Time limits for recovery after acute compression in dogs. Arch Neur Psychiat 71:271–290.

57. Barron K D, S S Schreiber, J L Cova, M E Scheibly. 1977. Quantitativel cytochemistry of RNA in axotomized feline rubral neurons. Brain Res 130:469–481.

58. Le Gros Clark W E, G G Penman. 1934. The projection of retina in the lateral geniculate body. Proc R Soc London (Biol) 114:291–313.

59. Olton D E. 1990. Dementia: animal models of the cognitive impairment following damage to the basal forebrain chilinergic system. Brain Res Bull 25:499–502.

60. Price D L. 1986. New perspective on Alzheimer's disease. Annu Rev Neurosci 9:489–512.

61. Altar C A, C B Boylan, C Jackson, R M Lindsay, C Hyman. 1992. Brain-derived neurotrophic factor augments rotational behavior and nigrostriatal dopamine turnover in vivo. Proc Natl Acad Sci USA 89:11347–11351.

62. Mitsumoto H, K Ikeda, B Klinkosz, J M Cedarbaum, V Wong, R M Lindsay. 1994. Arrest of motor neuron disease in wobbler mice cotreated with CNTF and BDNF. Science 265:1107–1110.

We claim:

1. A composition comprising (a) a material that activates a nuclear hormone receptor, (b) a material that activates the second messenger response system, and (c) a material that elevates $Ca^{2+}$, wherein (a), (b), and (c) comprise at least two different materials.

2. A composition as claimed in claim 1, wherein the material that activates the nuclear hormone receptor activates the retinoic acid response system.

3. A composition as claimed in claim 2, wherein the material that activates the nuclear hormone receptor is a retinoid.

4. A composition as claimed in claim 3, wherein the material that activates the nuclear hormone receptor is all-trans-retinoic acid.

5. A composition as claimed in claim 1, wherein the material that activates the second messenger response system is cAMP.

6. A composition as in claim 3, wherein the material that activates the second messenger response system is cAMP.

7. A composition as claimed in claim 4, wherein the material that activates the second messenger response system is cAMP.

8. A composition as claimed in claim 1, wherein the material that elevates $Ca^{2+}$ is a calcium channel stimulator.

9. A composition as claimed in claim 3, wherein the material that elevates $Ca^{2+}$ is a calcium channel stimulator.

10. A composition as claimed in claim 8, wherein the calcium channel stimulator is potassium chloride.

11. A composition as claimed in claim 9, wherein the calcium channel stimulator is potassium chloride.

12. A composition a claimed in claim 1, comprising all-trans-retinoic acid, cAMP, and KCl.

13. A method for inducing expression of at least one of trkB and trkC in an animal, comprising administering to the animal the composition of claim 1.

14. A method for inducing expression of at least one of trkB and trkC in an animal, comprising administering to the animal the composition of claim 3.

15. A method for inducing expression of at least one of trkB and trkC in an animal, comprising administering to the animal the composition of claim 5.

16. A method for inducing expression of at least one of trkB and trkC in an animal, comprising administering to the animal the composition of claim 6.

17. A method for inducing expression of at least one of trkB and trkC in an animal, comprising administering to the animal the composition of claim 8.

18. A method for inducing expression of at least one of trkB and trkC in an animal, comprising administering to the animal the composition of claim 9.

19. A method for inducing expression of at least one of trkB and trkC in an animal, comprising administering to the animal the composition of claim 14.

* * * * *

UNITED STATES PATENT AND TRADEMARK OFFICE
CERTIFICATE OF CORRECTION

PATENT NO. : 5,880,153
DATED : March 9, 1999
INVENTOR(S) : Toomas Neuman, et al.

It is certified that error appears in the above-identified patent and that said Letters Patent is hereby corrected as shown below:

On the title page, insert the following:

— Related U.S. Application Data
--[60] Provisional application No.60/135,108, Nov. 13, 1995.--.

In Column 1, line 9, please delete "a provisional application" and insert --provisional application No. 60/135,108--.

In Claim 12, at Column 15, line 1, after "12. A composition", please delete "a" and insert as--.

Signed and Sealed this

Twenty-first Day of March, 2000

Q. TODD DICKINSON

Attest:

Attesting Officer

Commissioner of Patents and Trademarks